US011224359B2

(12) United States Patent
Song et al.

(10) Patent No.: US 11,224,359 B2
(45) Date of Patent: Jan. 18, 2022

(54) REPETITIVE HUMAN ACTIVITIES ABNORMAL MOTION DETECTION

(71) Applicant: Robert Bosch GmbH, Stuttgart (DE)

(72) Inventors: Huan Song, San Jose, CA (US); Liu Ren, Cupertino, CA (US); Lincan Zou, San Jose, CA (US)

(73) Assignee: Robert Bosch GmbH, Stuttgart (DE)

( * ) Notice: Subject to any disclaimer, the term of this patent is extended or adjusted under 35 U.S.C. 154(b) by 89 days.

(21) Appl. No.: 16/717,285

(22) Filed: Dec. 17, 2019

(65) Prior Publication Data

US 2021/0177307 A1 Jun. 17, 2021

(51) Int. Cl.
*A61B 5/11* (2006.01)
*G06K 9/00* (2006.01)
*G06F 3/01* (2006.01)

(52) U.S. Cl.
CPC ........ *A61B 5/1118* (2013.01); *G06K 9/00335* (2013.01); *G06F 3/017* (2013.01)

(58) Field of Classification Search
CPC .... A61B 5/1118; G06K 9/00335; G06F 3/017
USPC ....................................................... 600/595
See application file for complete search history.

(56) References Cited

U.S. PATENT DOCUMENTS

| 9,137,309 | B2 * | 9/2015 | Ananny | G01C 25/00 |
| 2015/0023590 | A1 * | 1/2015 | Fahn | G06K 9/00335 |
| | | | | 382/160 |
| 2016/0249832 | A1 * | 9/2016 | Carter | A61B 5/7246 |
| | | | | 600/595 |
| 2017/0251972 | A1 * | 9/2017 | Jayaraman | A61B 5/6806 |
| 2018/0365089 | A1 * | 12/2018 | Okanohara | G06F 11/07 |
| 2019/0205771 | A1 * | 7/2019 | Lin | G06F 40/30 |
| 2019/0366154 | A1 * | 12/2019 | Callaghan | G16H 40/67 |

OTHER PUBLICATIONS

Fan, Quanfu, et al. "Recognition of repetitive sequential human activity." 2009 IEEE Conference on Computer Vision and Pattern Recognition. IEEE, 2009, Got It.
Krizhevsky, Alex, Ilya Sutskever, and Geoffrey E. Hinton. "Imagenet classification with deep convolutional neural networks." Advances in neural information processing systems. 2012, Got It.
Hochreiter, Sepp, and Jürgen Schmidhuber. "Long short-term memory." Neural computation 9.8 (1997): 11735-1780, Got It.

(Continued)

*Primary Examiner* — Omar Casillashernandez
(74) *Attorney, Agent, or Firm* — Brooks Kushman P.C.

(57) ABSTRACT

Abnormal motions are detected in sensor data collected with respect to performance of repetitive human activities. An autoencoder network model is trained based on a set of standard activity. Repetitive activity is extracted from sensor data. A first score is generated indicative of distance of a repetition of the repetitive activity from the standard activity. The repetitive activity is used to retrain the autoencoder network model, using weights of the autoencoder network model as initial values, the weights being based on the training of the autoencoder network model using the set of standard activity. A second score is generated indicative of whether the repetition is an outlier as compared to other repetitions of the repetitive activity. A final score is generated based on a weighting of the first score and the second score.

19 Claims, 4 Drawing Sheets

(56) References Cited

OTHER PUBLICATIONS

Song, Huan, et al. "Attend and diagnose: Clinical time series analysis using attention models." Thirty-Second AAAI Conference on Artificial Intelligence. 2018, Got It.
Baldi, Pierre. "Autoencoders, unsupervised learning, and deep architectures." Proceedings of ICML workshop on unsupervised and transfer learning. 2012, Got It.
Beggel, Laura, Michael Pfeiffer, and Bernd Bischl. "Robust Anomaly Detection in Images using Adversarial Autoencoders." arXiv preprint arXivi:1901.06355 (2019), Got It.
Williams, Graham, et al. "A comparative study of RN N for outlier detection in data mining." 2002 IEEE International Conference on Data Mining, 2002. Proceedings. IEEE, 2002, Got It.

\* cited by examiner

REPETITIVE HUMAN ACTIVITIES ABNORMAL MOTION DETECTION

TECHNICAL FIELD

The present disclosure relates to detection of abnormal motions in sensor data, where the sensor data is collected in relation to the performance of repetitive human activities.

BACKGROUND

With the increasing prevalence of the low-cost wearable sensors, such as accelerometer, gyroscope, and magnetometer sensors, large-scale human motion signals have become widely available. In order to analyze the motion data and further understand the underlying human activities, it is necessary to develop intelligent systems which are highly scalable and robust to different real-world scenarios.

One type of scenario which may be studied from such data is the category of motion signal analysis, where an activity under consideration is repetitive and cyclic in nature. Such type of data is common in many domains such as the workout routine for fitness exercise, the assembling operations for manufacturing and the cashier checkout at grocery store.

SUMMARY

According to one illustrative example, a method for detection of abnormal motions in sensor data collected with respect to performance of repetitive human activities includes training an autoencoder network model based on a set of standard activity; extracting repetitive activity from sensor data; generating a first score indicative of distance of a repetition of the repetitive activity from the standard activity; using the repetitive activity to retrain the autoencoder network model, using weights of the autoencoder network model as initial values, the weights being based on the training of the autoencoder network model using the set of standard activity; generating a second score indicative of whether the repetition is an outlier as compared to other repetitions of the repetitive activity; and generating a final score based on a weighting of the first score and the second score.

According to one illustrative example, a system for detecting abnormal motions in activity sequences, comprising a display device; a memory configured to store a motion analysis application; and a processor. The processor is operatively connected to the memory and the display device, and configured to execute the motion analysis application to train an autoencoder network model based on a set of standard activity; extract repetitive activity from sensor data; generating a first score indicative of distance of a repetition of the repetitive activity from the standard activity; using the repetitive activity to retrain the autoencoder network model, using weights of the autoencoder network model as initial values, the weights being based on the autoencoder network model as trained using the set of standard activity; generating a second score indicative of whether the repetition is an outlier as compared to other repetitions of the repetitive activity; and generating a final score based on a weighting of the first score and the second score.

According to one illustrative example, non-transitory computer readable medium comprising instructions of a motion analysis application that, when executed by one or more processors, cause the one or more processors to train an autoencoder network model based on a set of standard activity; extract repetitive activity from sensor data; generate a first score indicative of distance of a repetition of the repetitive activity from the standard activity; use the repetitive activity to retrain the autoencoder network model, using weights of the autoencoder network model as initial values, the weights being based on the autoencoder network model as trained using the set of standard activity; generate a second score indicative of whether the repetition is an outlier as compared to other repetitions of the repetitive activity; and generate a final score based on a weighting of the first score and the second score.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

An approach to systematically identify abnormal motions in repetitive activity is described. An important problem in analyzing the repetitive activities is to detect and locate the abnormal motions. The abnormalities can be characterized as differing significantly from the standard motions and/or from the rest of the repeating patterns. Note that the abnormal motions may occur at any time and in any duration. By successfully identifying and localizing the abnormal motions, attention of user may be drawn to the abnormality, and the user may be helped to improve the standardization in the future.

Understanding repetitive human activities from wearable sensor data is an important problem in fitness monitoring, manufacturing, retailing, and other physical activities. However, abnormality detection is challenging due for multiple reasons. As one reason, the motion variation across repetitions can be large. Although the overall pattern of a repetition may remain largely unchanged, short-duration motions are often susceptible to variation over time. These variations are easily confused with the true abnormalities, making it challenging for the algorithm to control false positive detections. As another challenge, as the activity continues for longer time, data drift is more likely to occur. Several factors can contribute to the drifting phenomenon, including internal sensor bias, environmental noise and muscle fatigue. In this scenario, comparing with the standard motion is no longer a valid criterion to determine the abnormality, since even normal motions will result in a large difference due to the drifted sensor readings.

In this disclosure, the above challenges are tackled by combining standardization evaluation and outlier detection under an autoencoder framework. While the evaluation step compares each motion only with a set of predefine standard motions, the outlier detector compares each motion with all other recorded motions in order to discover outlying samples. Each criterion is useful in identifying the true abnormalities and provides synergy to the other. Furthermore, an autoencoder neural network is used to fuse multiple sensors and/or modalities to derive the latent motion space, wherein the motions are represented by low-dimensional vectors and the two criteria are carried out. Compared to previous approaches which either considers only one criterion or operates on the raw signals, the proposed method is more robust to motion variation, data drift and incomplete reference.

Figure 1:
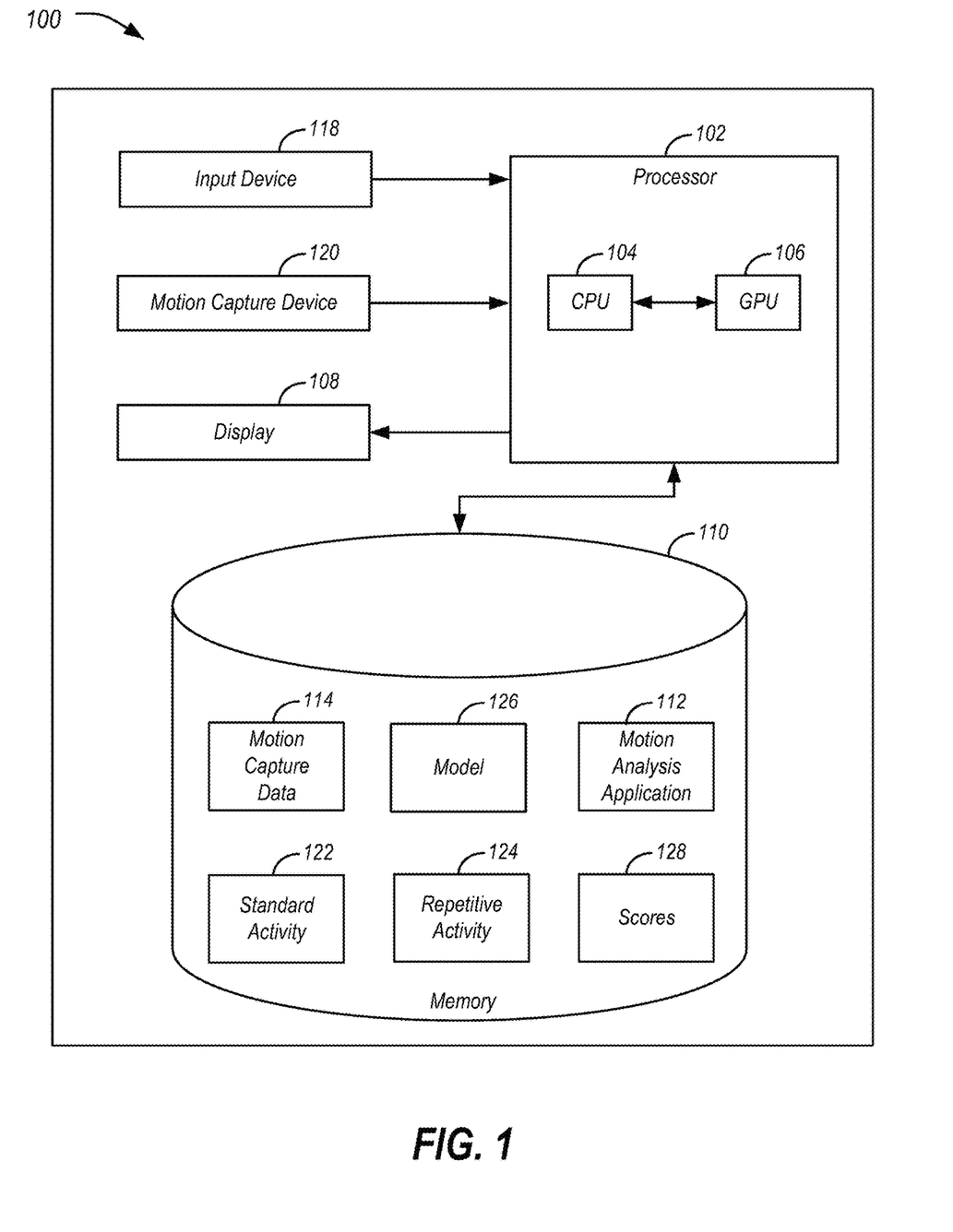
FIG. 1 is a schematic diagram of an exemplary embodiment of a system for detection of abnormal motions in sensor data collected with respect to the performance of repetitive human activities.

FIG. 1 is a schematic diagram of an exemplary embodiment of a system 100 for detection of abnormal motions in sensor data collected with respect to the performance of repetitive human activities. The system 100 includes a processor 102 that is operatively connected to a display device 108, a memory 110, an input device 118, and a motion capture device 120. As is described in more detail below, during operation, the system 100 (i) trains an autoencoder network model 126 based on a relatively small set of standard activity 122, (ii) extracts repetitive activity 124 from sensor data (e.g., motion capture data 114 from the motion capture device 120) to generate a first score 128 indicative of distance of the repetitions of the repetitive activity 124 from the standard activity 122, (iii) uses the repetitive activity 124 to retrain the autoencoder network model 126 while generating a second score 128 indicative of whether the repetition is an outlier, and (iv) generates a final score 128 based on a weighting of the first score 128 and the second score 128.

In the system 100, the processor 102 includes one or more integrated circuits that implement the functionality of a central processing unit (CPU) 104 and graphics processing unit (GPU) 106. In some examples, the processor 102 is a system on a chip (SoC) that integrates the functionality of the CPU 104 and GPU 106, and optionally other components including, for example, the memory 110, a network device, and a positioning system, into a single integrated device. In other examples the CPU 104 and GPU 106 are connected to each other via a peripheral connection device such as PCI express or another suitable peripheral data connection. In one example, the CPU 104 is a commercially available central processing device that implements an instruction set such as one of the x86, ARM, Power, or MIPS instruction set families.

The GPU 106 may include hardware and software for display of at least two-dimensional (2D) and optionally three-dimensional (3D) graphics to a display device 108. The display device 108 may include an electronic display screen, projector, printer, or any other suitable device that reproduces a graphical display. In some examples, processor 102 executes software programs including drivers and other software instructions using the hardware functionality in the GPU 106 to accelerate generation and display of the graphical depictions of models of human movement and visualizations of quantitative computations that are described herein During operation, the CPU 104 and GPU 106 execute stored program instructions that are retrieved from the memory 110. The stored program instructions include software that control the operation of the CPU 104 and the GPU 106 to perform the operations described herein.

While FIG. 1 depicts the processor 102 as including both the CPU 104 and GPU 106, alternative embodiments may omit the GPU 106, as for example the processor 102 may be of a server that generates output visualization data using only a CPU 104 and transmits the output visualization data to a remote client computing device that uses a GPU 106 and a display device 108 to display the data. Additionally, alternative embodiments of the processor 102 can include microcontrollers, application specific integrated circuits (ASICs), field programmable gate arrays (FPGAs), digital signal processors (DSPs), or any other suitable digital logic devices in addition to or as replacements of the CPU 104 and GPU 106.

In the system 100, the memory 110 includes both non-volatile memory and volatile memory devices. The non-volatile memory includes solid-state memories, such as NAND flash memory, magnetic and optical storage media, or any other suitable data storage device that retains data when the system 100 is deactivated or loses electrical power. The volatile memory includes static and dynamic random-access memory (RAM) that stores program instructions and data, including a motion analysis application 112, motion capture data 114, standard activity 122, repetitive activity 124, a model 126, and scores 128, during operation of the system 100. In some embodiments the CPU 104 and the GPU 106 each have access to separate RAM devices (e.g., a variant of DDR SDRAM for the CPU 104 and a variant of GDDR, HBM, or other RAM for the GPU 106) while in other embodiments the CPU 104 and GPU 106 access a shared memory device. The memory 110 may store the motion analysis application 112, motion capture data 114, standard activity 122, repetitive activity 124, model 126, and scores 128 for maintenance and retrieval.

The input device 118 may include any of various devices that enable the system 100 to receive the motion capture data 114, motion analysis application 112, and standardized evaluation results 116. Examples of suitable input devices include human interface inputs such as keyboards, mice, touchscreens, voice input devices, and the like, as well. In some examples the system 100 implements the input device 118 as a network adapter or peripheral interconnection device that receives data from another computer or external data storage device, which can be useful for receiving large sets of motion capture data 114 in an efficient manner.

The motion analysis application 112 includes instructions that, when executed by the processor 102 of the system 100, cause the system 100 to perform the processes and operations described herein.

The motion capture data 114 refers to a plurality of records representative of the locations of at least one tracked item or portion of the item over time. For example, the motion capture data 114 may include one or more of: records of positions of a reference point on a body part over time or at set time intervals, sensor data taken over time, a video stream or a video stream that has been processed using a computer-vision technique, data indicative of the operating state of a machine over time, etc. In some cases, the motion capture data 114 may include data representative of more than one continuous movement. For instance, the motion capture data 114 may include a combination of a plurality of combined motion capture data 114 sets. The motion capture data 114 may also include processed movement data, such as, for example, frame, step, cycle, and time information gleaned from the raw movement data.

A motion capture device 120 is a device configured to generate the motion capture data 114. Motion capture devices 120 may include, as some non-limiting examples: cameras, visual sensors, infra-red sensors, ultrasonic sensors, accelerometers, pressure sensors, or the like. One non-limiting example of a motion capture device 120 is one or a pair of digital gloves that a user wears while performing repetitive movements. The digital gloves may include a plurality of sensors that, in combination, capture various aspects of the motion of the user to generate the motion capture data 114. In an example, the motion capture data 114 may be received from the motion capture device 120 and stored in the memory 110.

An activity is an action performed by a user. Example of such activities are fitness exercises, assembling operations for manufacturing, cashier checkout operations at a store. A standard activity 122 may refer to a baseline or canonical version of the movement embodied in the activity. For instance, the standard activity 122 may be indicated by data that is indicative of correct performance of the fitness exercise, assembly operation, or checkout operation. The standard activity 122 may be used as a point of comparison for other movements. This may allow for identification of how close the other movements are to the standard activity 122. The repetitive activity 124 may refer to such other movements, and may include one or more repetitions of the activity performed by the user. If data indicative of the other movement is similar to data for the standard activity 122 then the movement may be considered to be correctly performed. If, however, the data differs, then the movement may be considered to be incorrectly performed. In an example, the standard activity 122 and/or the repetitive activity 124 may be observed and/or recorded by the motion capture device 120.

In artificial intelligence (AI) or machine learning systems, model-based reasoning refers to an inference method that operates based on a machine learning model 126. Generally, the machine-learning model 126 is trained to learn a function that provides a precise correlation between input values and output values. At runtime, a machine-learning engine uses the knowledge encoded in the machine-learning model 126 against observed data to derive conclusions such as a diagnosis or a prediction. In examples described herein, the model 126 employs an autoencoder architecture. An autoencoder is a type of machine-learning model that performs unsupervised learning on data to identify a relevant representation, or encoding, for the data that excludes elements that are deemed to be extraneous. From this dimensionally-reduced encoding, the autoencoder further attempts to regenerate an approximation of the original input, with an intent for the regenerated output to match the original input as closely as possible. Thus, an autoencoder includes both encoder and decoder aspects.

The scores 128 refer to values that are computed using the model 126 that are indicative of likelihood of a match of an instance of a repetitive activity 124 to a reference standard activity 122. As used herein, these scores 128 may indicate distance of a repetitive activity 124 to the reference standard activity 122, an indication of whether the instance of the repetitive activity 124 is an outlier as compared to other instances of the repetitive activity 124, and/or a weighted average of these two types of scores.

Figure 2:
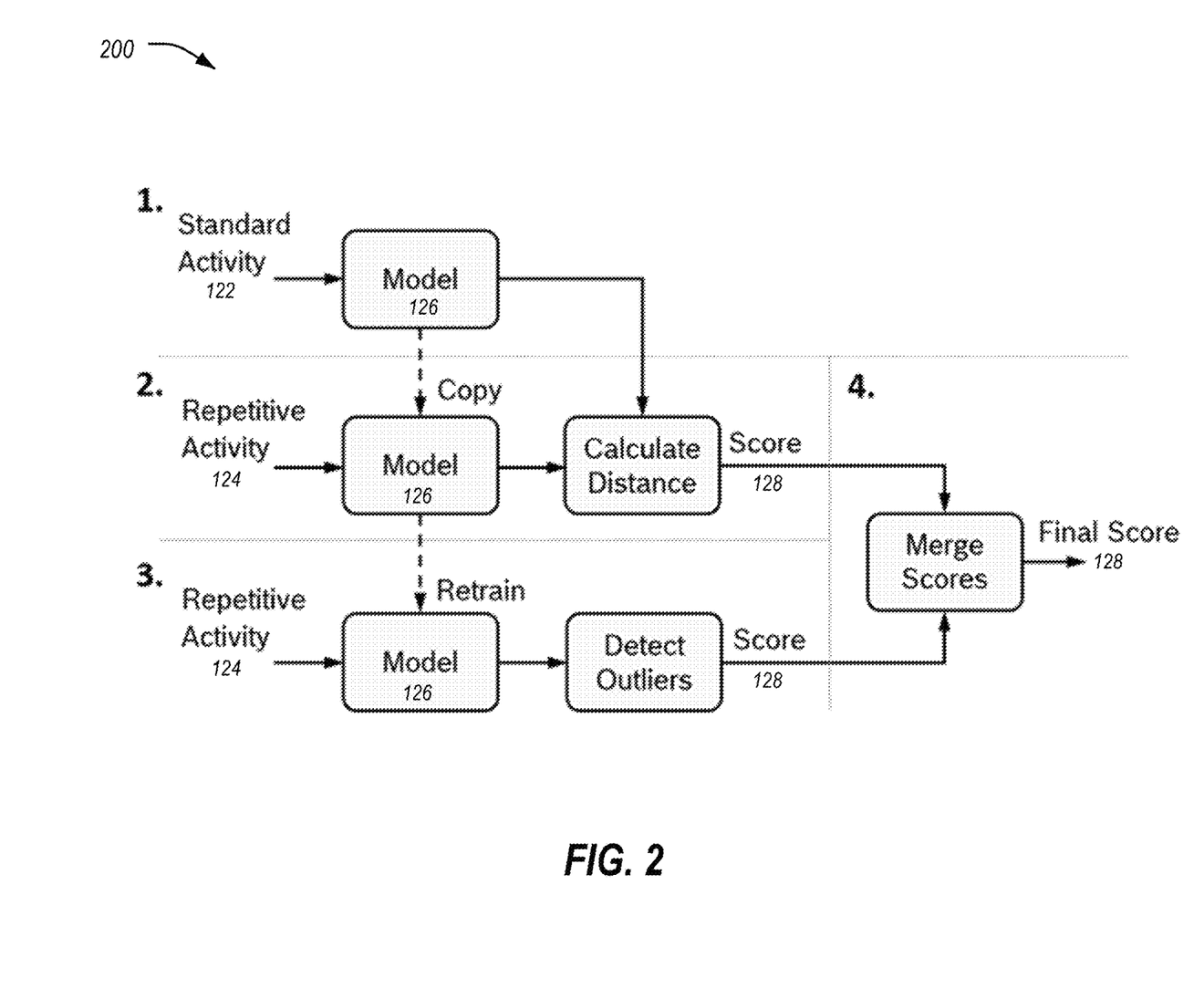
FIG. 2 illustrates an example operational overview of a process to detect abnormalities in repetitive activity.

FIG. 2 illustrates an example operational overview of a process 200 to detect abnormalities in repetitive activity. Referring to FIG. 2, and with continued reference to the system 100 of FIG. 1, the process 200 includes four main operations. First, the model 126 is trained based on a small set of standard activity 122. Generally, the encoder of the model 126 learns to extract low-dimensional motion representations, while the decoder of the model 126 learns to reconstruct the input motions from the representations. The motion representations may be stored as a set of standard activity 122 references.

Second, at use time, the representations for the repetitive activity 124 are extracted. In an example, these representations may be extracted from data collected from the motion capture device 120. Each of the motions is compared with the reference set and an abnormality score 128 is calculated where a large value corresponds to higher likelihood of an abnormal motion.

Third, after the recording completes, the recorded motions (e.g., excluding the standard activity 122 reference) are used to retrain the autoencoder network model 126. The resulting motion representations are compared in a pair-wise fashion in order to discover the outliers as abnormality. Another abnormality score 128 is calculated based on the distances to close neighbors.

Finally, the scores 128 for the second and third operations are combined based on a weighting parameter to calculate the motion abnormality. This final weighted score 128 may accordingly be used in the identification of abnormal motions.

Details of the model 126 and operations of the process 200 are discussed in further detail below. Table 1 summarizes certain notations that are used throughout the discussion of the model 126 and the operations of the process 200:

TABLE 1

| Notations | |
|---|---|
| Notation | Denotes |
| i | Index of the motion window in standard activity |
| j | Index of the motion window in the repetitive activity during use time |
| k, K | Index of the sensor and total number of sensors |
| x | Extracted motion window |
| z | Extracted latent representation for the corresponding motion window |

Figure 3:
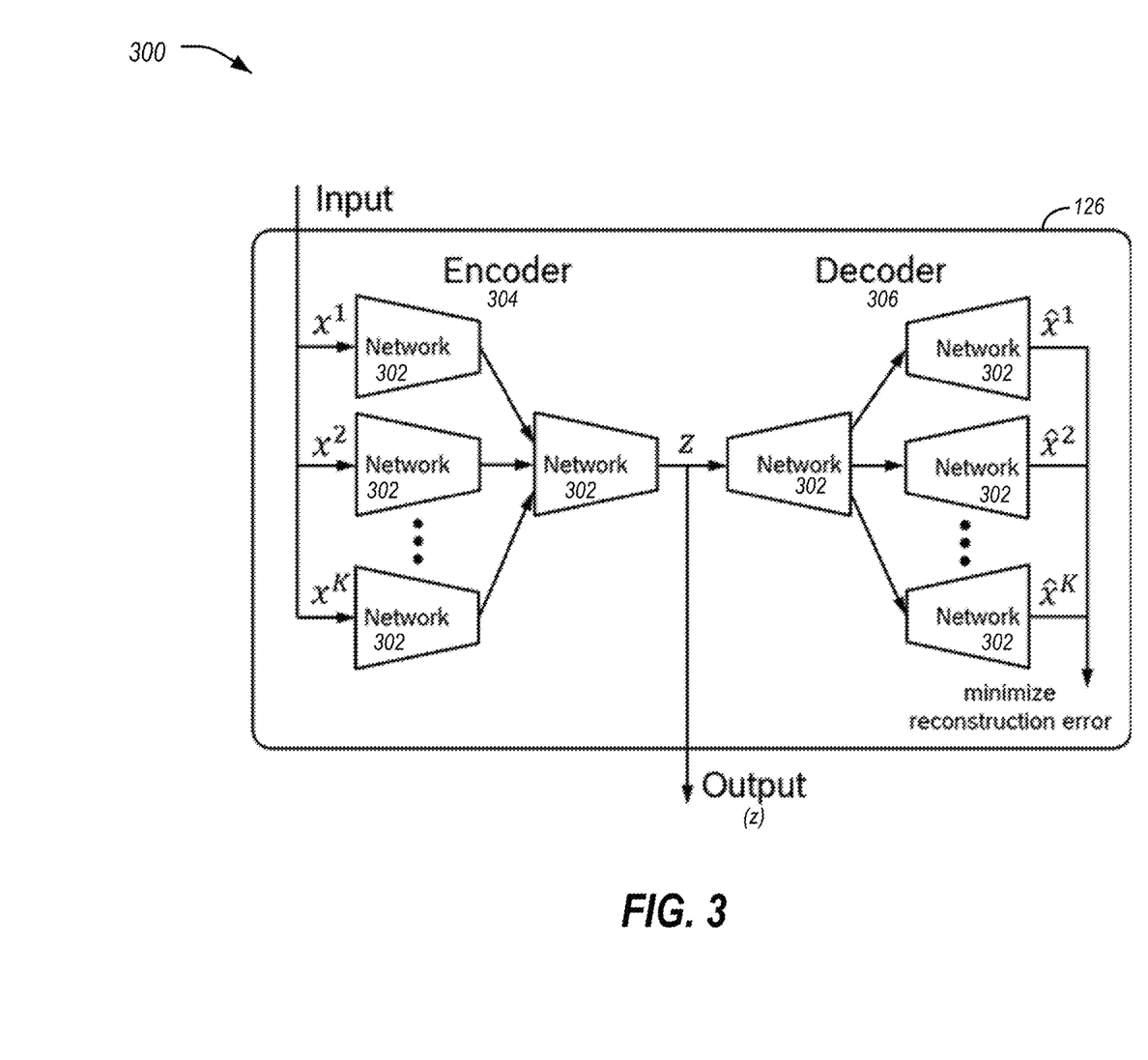
FIG. 3 illustrates an example detail of the model based on an autoencoder architecture.

FIG. 3 illustrates an example detail of the model 126 based on an autoencoder architecture. As shown, each trapezoid block denotes a neural sub-network 302. As mentioned above, the autoencoder model 126 includes an encoder 304 and a decoder 306. The encoder 304 further includes of multiple sub-networks 302. Every sub-network 302 structure of the encoder 304 is mirrored with a corresponding sub-network 302 of the decoder 306 to constitute the overall decoder 206. As shown on the encoder 304 side, the input includes extracted motion windows x for each of K sensors (e.g., of the motion capture device 120). Each of the K sensor inputs is applied to a different one of the sub-networks 302, which in-turn feed into one or more further layers, which provide an extracted motion window output z. On the decoder 306 side, the extracted motion window output z is fed through the mirrored decoder 306 to regenerate estimated motion windows $\hat{x}$ which attempt to minimize the reconstruction error.

Figure 4:
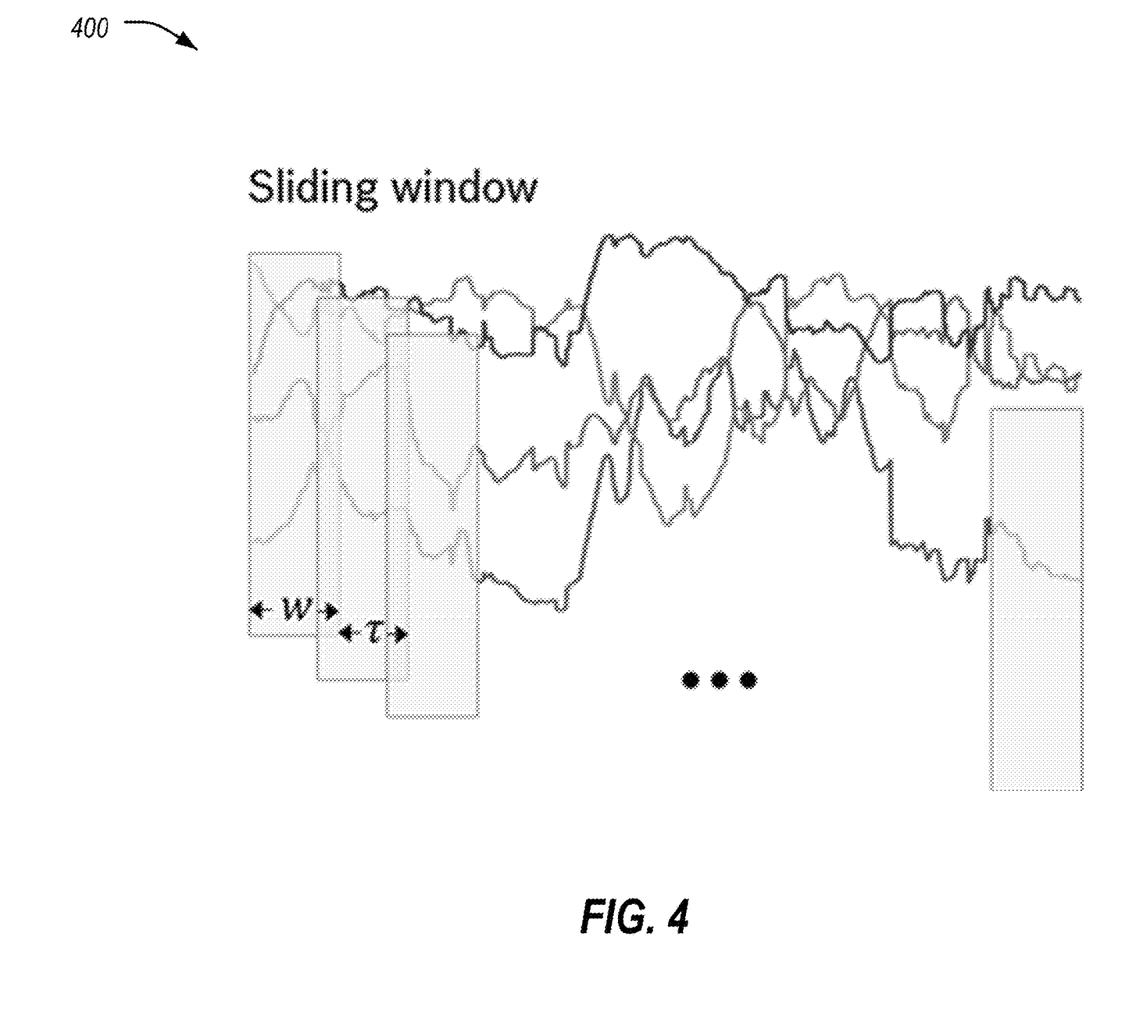
FIG. 4 illustrates an example sliding window approach for temporal segmentation.

With respect to the first main operation, that of autoencoder model 126 training on standard activity 122, the following example implementation is provided. The user records a few cycles of the standard activity 122 as reference prior to using the system 100. Based on the recording of the standard activity 122, temporal segmentation is then performed using a sliding window in order to capture the short-duration motion patterns. Denoting the window length as w and the stride of the moving window as $\tau$, the temporal segmentation process may be illustrated as shown in FIG. 4. Since multiple types of sensor and multiple placements may exist, the temporal segmentation is performed for every existing sensor. Denoting the number of sensors as K and the length of the standard activity 122 recording as $l_{std}$, the number of the motion windows for each sensor as a result of the segmentation is $N_i=(l_{std}-w)/\tau+1$ and the total number of motion windows for all sensors is $N_i \times K$.

Using the motion windows as input data, the autoencoder neural network model 126 including the encoder 304 and the decoder 306 is trained, as visualized in FIG. 2. As can be seen, the encoder 304 contains multiple sub-networks 302, where, in the illustrated example, each sensor is first processed by a separate sub-network 302 and all sensors are then fused via another sub-network 302. The sub-network 302 may utilize any network structure that is appropriate to the application, including a fully-connected network, a convolutional neural network (e.g., as discussed in Krizhevsky, Alex, Ilya Sutskever, and Geoffrey E. Hinton. "Imagenet classification with deep convolutional neural networks." *Advances in neural information processing systems.* 2012), a long short-term memory network (e.g., as discussed in Hochreiter, Sepp, and Jürgen Schmidhuber. "Long short-term memory." *Neural computation* 9.8 (1997): 1735-1780) and an attention network (e.g., as discussed in Song, Huan, et al. "Attend and diagnose: Clinical time series analysis using attention models." *Thirty-Second AAAI Conference on Artificial Intelligence.* 2018). The mirrored layers then constitute the decoder 306 part. The overall network parameters are learned through backpropagation algorithm by minimizing the following mean squared error loss (e.g., as discussed in Baldi, Pierre. "Autoencoders, unsupervised learning, and deep architectures." *Proceedings of ICML workshop on unsupervised and transfer learning.* 2012), as shown in Equation (1):

$$L = \frac{1}{KN_i}\sum_{k=1}^{K}\sum_{i=1}^{N_i} \|x_i^k - \hat{x}_i^k\|_2^2 \qquad (1)$$

Where $\hat{x}_i^k$ denotes the reconstructed motion window at the output of decoder for window i of sensor k.

With continued reference to FIG. 3, after the model 126 is trained, the input windows of the standard activity 122 $\{x_i^k\}_{k=1}^{K}$ are fed to the encoder 304, and the latent representations are extracted from the bottleneck layer $z_i$ as the output. These representations contain fused motion feature corresponding to the input windows. Note that the following steps in the described system 100 also follow this framework, and the abnormality score 128 calculations will be performed in the latent space.

The effects of the autoencoder neural network model 126 are two-folds: first, it fuses the measurements of multiple sensors to derive a concise and rich representation which is more robust to sensor noise and motion variation. Second, depending on the specific network structure, the encoder 304 is able to extract different levels of temporal dependencies which are more suitable than the raw measurements in characterizing the motion window.

Standardization evaluation may then be performed after the autoencoder training on standard activity 122 is complete. After the reference standard activity 122 is provided and the first operations are complete, the user may start using the system 100. In the standardization evaluation step, the trained model 126 of the first operations may be copied, and the latent representations for each motion window $x_j$ in the data stream may be extracted. These latent representations are then compared with all representations $z_i$'s from the reference, and the abnormality score 128 is calculated as shown in Equation (2):

$$s_{std} = \min_{i}\|z_j - z_i\|_2 \qquad (2)$$

The first two operations constitute the standardization evaluation criterion. As mentioned above, although this criterion is straightforward to implement, it is likely to fail when the sensor recording is drifted or when the pre-defined set of normal motions is incomplete. Thus, the system 100 further incorporates an outlier detection procedure in the next operation to address this challenge.

With continuing reference to FIG. 2, the third operation relates to the retraining of the autoencoder model 126 on repetitive activities 124 and outlier detection. When the recording completes, the repetitive activity 124 data may be exploited by retraining the autoencoder model 126. Denoting the number of motion windows in the recording as $N_1$, the autoencoder model 126 weights from operation two may be utilized as initialization. The network parameters may then be updated with the set $\{x_j\}_{j=1}^{N_j}$. Note that the sensor index k is omitted for clarity.

The resulting motion latent space from retraining enables the detection of the abnormalities as outliers. The outlying samples can be considered as having significantly different features from all other samples. According to this intuition, for a sample $x_j$, a distance is first calculated to all other recorded motion windows within the latent space and then an abnormality score is defined for the instant motion window based on the nearest neighbors, as shown in Equation (3):

$$s_{rep} = \frac{1}{M}\sum_{m=1}^{M} \|z_j - z_m\|_2 \qquad (3)$$

where M denotes the number of nearest neighbors to consider, with itself excluded.

Thus, even when data drift or a novel motion undefined in the reference occurs, a normal motion still repeats due to the repetitive nature of the activity, while abnormal motions are rare and likely to be different each time they appear. The overall retraining and outlier detection process is shown as operation three in FIG. 2.

Moving to operation four, the abnormality scored determined at operation three are merged. It is worth noting that the outlier detection and the standardization evaluation stages are complementary and in some cases indispensable to each other. On one hand, comparing only to the reference standard activity 122 motions is likely to suffer when data drifting happens or when the definition is incomplete. On the other hand, outlier detection cannot act as the sole criteria either. Consider a corner case where the user mistakes an abnormal motion as normal and therefore still repeats it many times. The outlier detector will likely identify several close neighbors and return a low abnormality score, thus producing false negatives. Contrarily, the standardization evaluator is unaffected and able to identify high abnormality score each time the motion occurs.

Therefore, it is critical to jointly consider the two criteria by unifying their respective abnormality scores 128. The final abnormality score 128 may therefore be calculated as shown in Equation (4):

$$s = \lambda \times s_{std} + (1-\lambda) \times s_{rep} \quad (4)$$

Where the parameter $\lambda$ balances the two criterion and can be determined based on either the confidence in the reference standard activity 122 or the likelihood of sensor drifting.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method for detection of abnormal motions in sensor data collected with respect to performance of repetitive human activities, comprising:

training an autoencoder network model based on a set of standard activity;

extracting repetitive activity from sensor data;

using the autoencoder network model, generating a first score indicative of distance of a repetition of the repetitive activity from the standard activity;

using the repetitive activity to retrain the autoencoder network model, using weights of the autoencoder network model as initial values, the weights being based on the training of the autoencoder network model using the set of standard activity;

using the autoencoder network model as retrained, generating a second score indicative of whether the repetition is an outlier as compared to other repetitions of the repetitive activity; and generating a final score based on a weighting of the first score and the second score.

2. The method of claim 1, further comprising:

applying each of a plurality of sensor inputs of the sensor data to a corresponding one of a plurality of encoder sub-networks of an encoder of the autoencoder network model;

applying outputs of the plurality of encoder sub-networks to a further encoder sub-network of the encoder to fuse the plurality of sensor inputs to generate an extracted motion window output; and applying the extracted motion window output to a decoder of the autoencoder network mode, the decoder including a set of decoder sub-networks mirroring the plurality of encoder sub-networks, the decoder regenerating estimated motion windows to minimize reconstruction error comparted to the plurality of sensor inputs.

3. The method of claim 2, further comprising learning parameters of the encoder sub-networks and the decoder sub-networks through backpropagation by minimizing mean-squared error loss.

4. The method of claim 2, wherein the sub-networks include one or more of a fully-connected network, a convolutional neural network, a long short-term memory network, or an attention network.

5. The method of claim 1, further comprising determining the weighting of the first score and the second score according to one or more of a confidence in the distance of a repetition of the repetitive activity from the standard activity or a likelihood of sensor drifting of sensors generating the sensor data.

6. The method of claim 1, wherein the sensor data is motion capture data captured from a wearable glove motion capture device.

7. The method of claim 1, wherein the repetitive human activities include one or more of a fitness exercise, a manufacturing assembly operation, or a store checkout operation.

8. A system for detecting abnormal motions in activity sequences, comprising:

a display device;

a memory configured to store a motion analysis application; and a processor, operatively connected to the memory and the display device, and configured to execute the motion analysis application to train an autoencoder network model based on a set of standard activity;

extract repetitive activity from sensor data;

using the autoencoder network model, generating a first score indicative of distance of a repetition of the repetitive activity from the standard activity;

using the repetitive activity to retrain the autoencoder network model, using weights of the autoencoder network model as initial values, the weights being based on the autoencoder network model as trained using the set of standard activity;

using the autoencoder network model as retrained, generating a second score indicative of whether the repetition is an outlier as compared to other repetitions of the repetitive activity; and generating a final score based on a weighting of the first score and the second score.

9. The system of claim 8, wherein the processor is further configured to execute the motion analysis application to:

apply each of a plurality of sensor inputs of the sensor data to a corresponding one of a plurality of encoder sub-networks of an encoder of the autoencoder network model;

apply outputs of the plurality of encoder sub-networks to a further encoder sub-network of the encoder to fuse the plurality of sensor inputs to generate an extracted motion window output; and apply the extracted motion window output to a decoder of the autoencoder network mode, the decoder including a set of decoder sub-networks mirroring the plurality of encoder sub-networks, the decoder regenerating estimated motion windows to minimize reconstruction error comparted to the plurality of sensor inputs.

10. The system of claim 9, wherein the processor is further configured to execute the motion analysis application to learn parameters of the encoder sub-networks and the decoder sub-networks through backpropagation by minimizing mean-squared error loss.

11. The system of claim 9, wherein the sub-networks include one or more of a fully-connected network, a convolutional neural network, a long short-term memory network, or an attention network.

12. The system of claim 8, wherein the processor is further configured to execute the motion analysis application to determine the weighting of the first score and the second score according to one or more of a confidence in the distance of a repetition of the repetitive activity from the standard activity or a likelihood of sensor drifting of sensors generating the sensor data.

13. The system of claim 8, further comprising a wearable glove motion capture device, wherein the sensor data is motion capture data captured from the wearable glove motion capture device.

14. A non-transitory computer readable medium comprising instructions of a motion analysis application that, when executed by one or more processors, cause the one or more processors to:

train an autoencoder network model based on a set of standard activity;

extract repetitive activity from sensor data;

use the autoencoder network model to generate a first score indicative of distance of a repetition of the repetitive activity from the standard activity;

use the repetitive activity to retrain the autoencoder network model, using weights of the autoencoder network model as initial values, the weights being based on the autoencoder network model as trained using the set of standard activity;

use the autoencoder network model, as retrained, to generate a second score indicative of whether the repetition is an outlier as compared to other repetitions of the repetitive activity; and generate a final score based on a weighting of the first score and the second score.

15. The medium of claim 14, further comprising instructions of the motion analysis application that, when executed by the one or more processors, cause the one or more processors to:

apply each of a plurality of sensor inputs of the sensor data to a corresponding one of a plurality of encoder sub-networks of an encoder of the autoencoder network model;

apply outputs of the plurality of encoder sub-networks to a further encoder sub-network of the encoder to fuse the plurality of sensor inputs to generate an extracted motion window output; and apply the extracted motion window output to a decoder of the autoencoder network mode, the decoder including a set of decoder sub-networks mirroring the plurality of encoder sub-networks, the decoder regenerating estimated motion windows to minimize reconstruction error comparted to the plurality of sensor inputs.

16. The medium of claim 15, further comprising instructions of the motion analysis application that, when executed by the one or more processors, cause the one or more processors to learn parameters of the encoder sub-networks and the decoder sub-networks through backpropagation by minimizing mean-squared error loss.

17. The medium of claim 15, wherein the sub-networks include one or more of a fully-connected network, a convolutional neural network, a long short-term memory network, or an attention network.

18. The medium of claim 14, further comprising instructions of the motion analysis application that, when executed by the one or more processors, cause the one or more processors to determine the weighting of the first score and the second score according to one or more of a confidence in the distance of a repetition of the repetitive activity from the standard activity or a likelihood of sensor drifting of sensors generating the sensor data.

19. The medium of claim 14, wherein the sensor data is motion capture data captured from a wearable glove motion capture device.

* * * * *